United States Patent [19]

Saville

[11] Patent Number: Plant 6,507

[45] Date of Patent: Jan. 3, 1989

[54] ROSE PLANT NAMED SAVAMIST

[75] Inventor: F. Harmon Saville, Rowley, Mass.

[73] Assignee: Nor'East Miniature Roses, Inc., Rowley, Mass.

[21] Appl. No.: 26,527

[22] Filed: Mar. 16, 1987

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new unusual Apricot miniature rose.

1 Drawing Sheet

1

The present invention relates to a new and distinct variety of rose plant of the miniature rose class, which was originated by my crossing as seed parent the variety known as "Fantasia" (U.S. Plant Pat. No. 590) and as pollen parent the rose known as "Baby Katie". The denomination of this new rose is "Savamist".

Among the novel characteristics possessed by this new variety which distinguish it from its parents and all other varieties of which I am aware are its unusual Apricot flowers which are long lasting on the plant and after cutting. Flower coloring varies from Brick Red in exhibition stage to Apricot after opening. Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "32A" is plate 32A of The Royal Horticultural Society Colour Chart.

Parentage: Seedling.

*Seed parent.*—"Fantasia".

*Pollen parent.*—"Baby Katie".

Class: Miniature.

The following observations are made of specimens grown outdoors in San Bernardino County, Calif., during the month of January.

FLOWER

Blooming habit: Continuous.

A. Bud:

(1) *Size.*—Medium.

(2) *Form.*—Ovate.

(3) *Color.*—As sepals divide, bud color is near Nasturtium Red 32B.

(4) Sepals.—Usually non-foliated, longer than bud, smooth.

(5) *Peduncle.*—Length — about one inch. Aspect — straight. Strength — erect. Color — near 138B flushed with 181B.

2

B. Bloom:

(1) *Size.*—Average size when fully expanded — about $\frac{3}{8}$ inch.

(2) *Borne.*—Singly, one to a stem, and together in large sprays.

(3) *Form.*—High centered at first, becoming flat. Outer petals tend to pointed apices and all petals tend to roll under; center holds well and flower has exhibition form.

(4) *Petalage.*—Number of petals under normal conditions — about 40 to 45.

(5) *Color.*—Flower coloring involves a range of hues and colors of varying tonality. After sepals fall and petals begin to unfurl, color of outer petal's undersurface initially visible is in the range of near Brick Red, 35B, at petal's edge washing or shading to near 32D and then to near 19C, and becoming near Primrose Yellow, 4D, at point of petal attachment. In one-third to one-half open stages, top surface of outer petals is near Brick Red embodying all hues from near 35D through near 35A, deepening in tone from outer petals toward flower center. However, when fully open and mature, flower coloring tends toward Apricot tones, ranging from Apricot, near 24D, at and near flower centers, to near 35C at outer petals.

C. Petals:

(1) *Texture.*—Thick.

(2) *Appearance.*—Inside velvety and outside satiny.

(3) *Form.*—Broad, fan shaped often with pointed apices.

(4) *Arrangement.*—Regularly arranged, imbricated.

(5) *Petaloids in center.*—Few.

(6) *Persistence.*—Drop off cleanly.

(7) *Fragrance.*—Slight.

(8) *Lasting quality.*—Very long lasting quality on plant and as cut flower.

REPRODUCTIVE ORGANS

A. Stamens, filaments and anthers:

*Arrangement and color.*—Regularly arranged around styles. Color — filaments near 17B.

B. Pollen:

*Color.*—Near 17A.

C. Styles: Even, medium length.

D. Stigmas:

*Color.*—Near 2D.

E. Hips: None observed.

PLANT

A. Form: Compact.

B. Growth: Very vigorous, uniform branching.
*Height attained.*—About 12 to 14 inches.

C. Foliage: Compound 5 to 7 leaflets.
(1) *Size.*—Medium.
(2) *Quantity*—Abundant.
(3) *Color.*—New foliage: Upper side —near 137A. Under side —near 138B. Old foliage: Upper side — near 137A. Under side — near to 138B.
(4) *Shape.*—Oval, pointed.
(5) *Texture.*—Upper side is glossy; under side is matte.
(6) *Edge.*—Serrate.
(7) *Serration.*—Regular, fine.
(8) *Leaf stem.*—Color — near to 187C. Under side — near 139D.
(9) *Stipules.*—Medium length, smooth.
(10) *Resistance to disease.*—Blackspot — Above average. Mildew — Average. Rust — Average.

D. Wood:
(1) *New wood.*—Color — near 146C. Bark — smooth.
(2) *Old wood.*—Color — near 141A. Bark — smooth.

E. Thorns:
(1) *Thorns.*—Quantity (main stalk) — ordinary. On laterals from stalk — few. Form — long, thin, straight points. Length — medium. Color — near 185A. Position — irregular.

F. Winter hardiness: Needs protection in severe climates.

I claim:

1. A new and distinct variety of rose plant of the miniature rose class, substantially as shown and described, characterized particularly by attractive flowers beginning as Brick Red blooms of good exhibition form which mature into fully open Apricot blossoms and which are long lasting on the plant and after cutting.

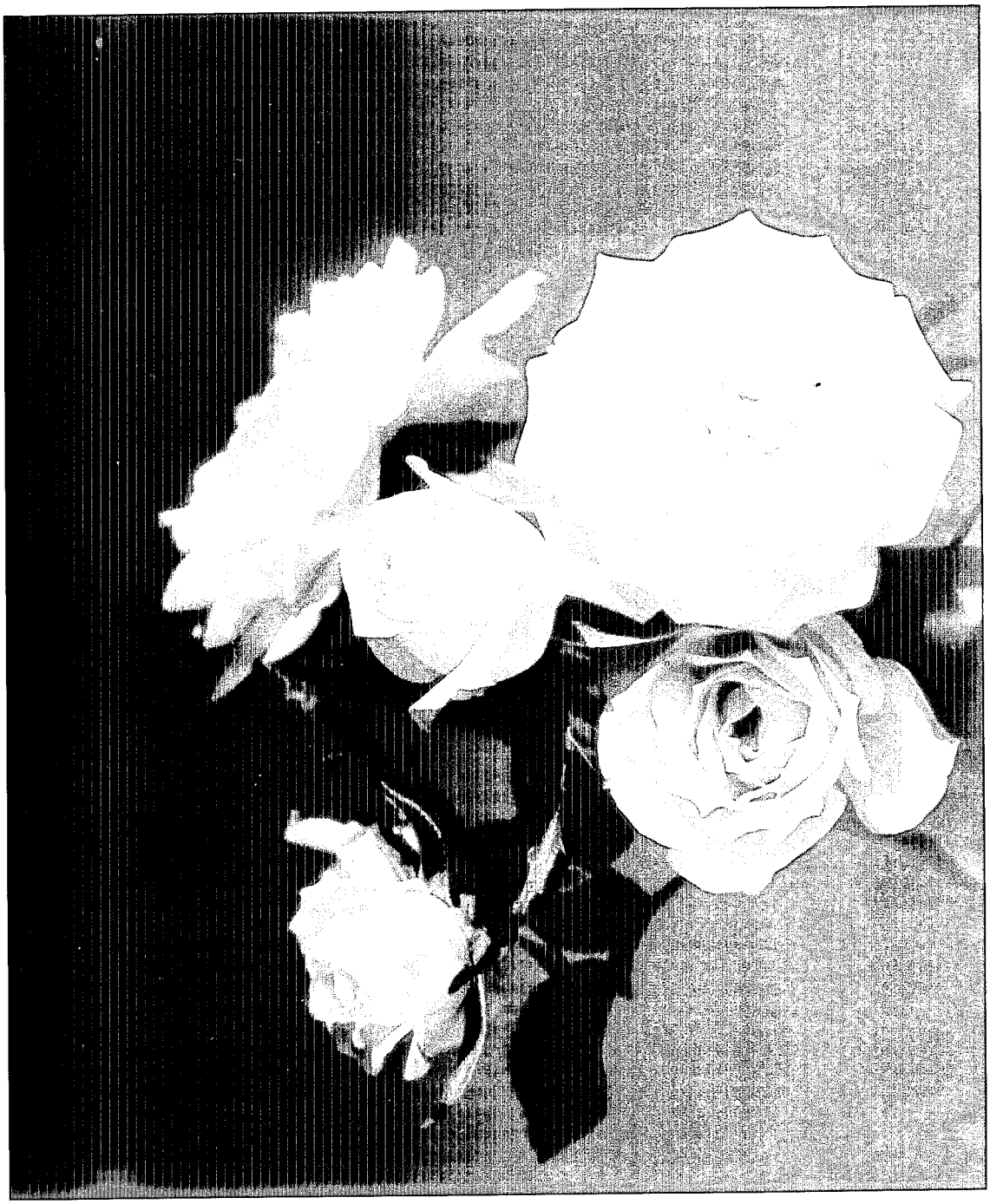

* * * * *